(12) United States Patent
de Laat et al.

(10) Patent No.: US 12,006,538 B2
(45) Date of Patent: Jun. 11, 2024

(54) 3-D GENOMIC REGION OF INTEREST SEQUENCING STRATEGIES

(75) Inventors: Wouter Leonard de Laat, Utrecht (NL); Max Jan van Min, The Hague (NL)

(73) Assignee: Cergentis BV, Utrecht (NL)

( * ) Notice: Subject to any disclaimer, the term of this patent is extended or adjusted under 35 U.S.C. 154(b) by 0 days.

(21) Appl. No.: 13/807,662

(22) PCT Filed: Jul. 8, 2011

(86) PCT No.: PCT/NL2011/050504
§ 371 (c)(1),
(2), (4) Date: Mar. 12, 2013

(87) PCT Pub. No.: WO2012/005595
PCT Pub. Date: Jan. 12, 2012

(65) Prior Publication Data
US 2013/0183672 A1  Jul. 18, 2013

Related U.S. Application Data

(60) Provisional application No. 61/362,778, filed on Jul. 9, 2010.

(51) Int. Cl.
*C12P 19/34* (2006.01)
*C12Q 1/6855* (2018.01)
*C12Q 1/6869* (2018.01)
*C07H 21/04* (2006.01)

(52) U.S. Cl.
CPC ......... *C12Q 1/6869* (2013.01); *C12Q 1/6855* (2013.01)

(58) Field of Classification Search
None
See application file for complete search history.

(56) References Cited

U.S. PATENT DOCUMENTS

| | | | | |
|---|---|---|---|---|
| 5,077,204 A * | 12/1991 | Brake | ................ | C07K 14/62 435/224 |
| 5,221,518 A * | 6/1993 | Mills | ................ | C12Q 1/6869 422/62 |
| 5,258,507 A * | 11/1993 | Cruickshank et al. | ................ | C07H 21/00 536/24.3 |
| 6,060,275 A * | 5/2000 | Hacohen | ................ | C07K 14/4702 435/69.1 |
| 6,060,644 A * | 5/2000 | Schnable | ................ | C07K 14/415 435/419 |
| 6,204,039 B1 * | 3/2001 | Allen et al. | ................ | C12N 9/88 435/6.15 |
| 6,291,168 B1 * | 9/2001 | Musso | ................ | C12Q 1/689 435/15 |
| 6,455,692 B1 * | 9/2002 | Gjerde | ................ | C12N 15/101 210/198.2 |
| 6,632,636 B1 * | 10/2003 | Lagace | ................ | C07K 14/212 435/189 |
| 2002/0119455 A1 * | 8/2002 | Chan | ................ | C12Q 1/6809 435/6.12 |
| 2003/0013863 A1 * | 1/2003 | Buchholz | ................ | C12P 19/34 536/23.1 |
| 2003/0054347 A1 * | 3/2003 | Richards | ................ | C07K 14/705 435/6.16 |
| 2003/0157705 A1 * | 8/2003 | Fodor | ................ | 435/325 |
| 2004/0014195 A1 * | 1/2004 | DeSantis | ................ | C12N 9/78 435/228 |
| 2004/0038401 A1 * | 2/2004 | Mead | ................ | C12N 15/66 435/455 |
| 2004/0142387 A1 * | 7/2004 | Lernmark | ................ | C12N 9/88 435/7.2 |
| 2005/0221341 A1 * | 10/2005 | Shimkets | ................ | C12Q 1/6813 435/6.11 |
| 2005/0221439 A1 * | 10/2005 | Bakaletz et al. | ................ | A61P 31/12 435/69.3 |
| 2005/0232900 A1 * | 10/2005 | Vogels et al. | ................ | C07K 14/005 424/93.2 |
| 2006/0073501 A1 * | 4/2006 | Van Den Boom | ................ | C12Q 2563/167 435/6.11 |
| 2006/0107345 A1 * | 5/2006 | Alexandrov et al. | ................ | C07K 14/415 800/278 |
| 2006/0150283 A1 * | 7/2006 | Alexandrov et al. | ................ | C07K 14/415 536/23.6 |
| 2006/0199183 A1 * | 9/2006 | Valat | ................ | C12Q 1/6837 435/6.12 |
| 2006/0223073 A1 * | 10/2006 | Boyes et al. | ................ | C12N 9/22 435/199 |

(Continued)

FOREIGN PATENT DOCUMENTS

| | | |
|---|---|---|
| CN | 101310024 A | 11/2008 |
| CN | 101688237 A | 3/2010 |

(Continued)

OTHER PUBLICATIONS

"Minimal homology requirements for PCR primers," Nucleic Acids Research, vol. 17, No. 16, 1989, p. 6749.*

(Continued)

*Primary Examiner* — Bradley L. Sisson
(74) *Attorney, Agent, or Firm* — Patent Law Works LLP

(57) ABSTRACT

The invention relates to methods for determining the sequence of a genomic region of interest comprising a target nucleotide sequence comprising, fragmenting a crosslinked DNA, ligating the fragmented cross linked DNA, reversing the crosslinking and determining at least part of the sequences of ligated DNA fragments which comprise a target nucleotide sequence.

16 Claims, 3 Drawing Sheets

Figure 1:
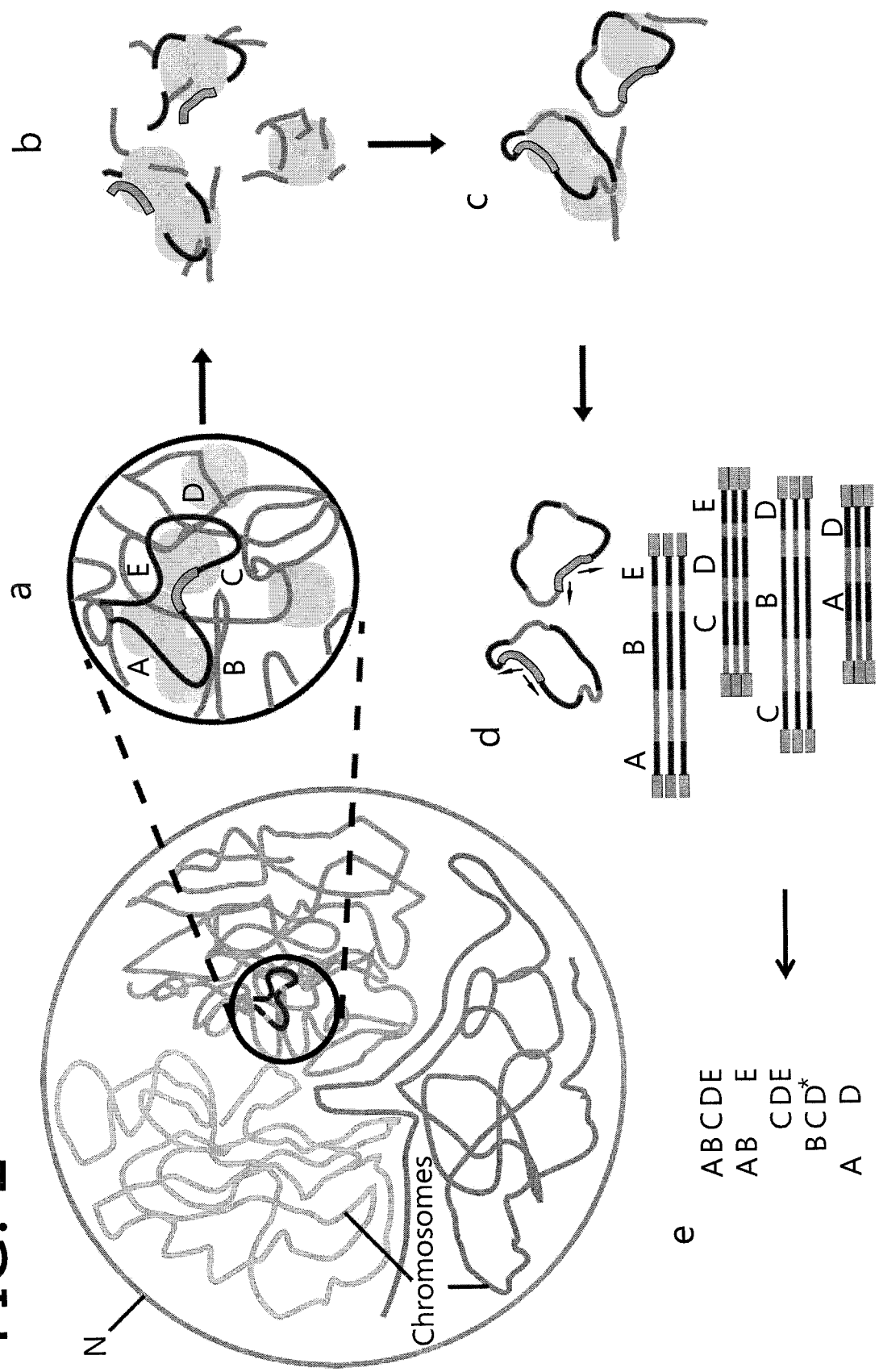

Specification includes a Sequence Listing.

(56) References Cited

U.S. PATENT DOCUMENTS

| | | | |
|---|---|---|---|
| 2006/0248617 A1* | 11/2006 | Manaka et al. | C12Q 1/02 435/6.15 |
| 2006/0292560 A1* | 12/2006 | Burgess | C12N 15/1034 435/6.12 |
| 2006/0292611 A1* | 12/2006 | Berka | C12N 15/10 435/6.11 |
| 2007/0031829 A1* | 2/2007 | Yasuno | C12Q 1/6886 435/6.12 |
| 2007/0042400 A1* | 2/2007 | Choi | C12N 15/10 435/6.12 |
| 2007/0042419 A1* | 2/2007 | Barany | C12Q 1/6813 435/6.12 |
| 2007/0048748 A1* | 3/2007 | Williams et al. | C12N 9/1252 435/6.12 |
| 2007/0072208 A1* | 3/2007 | Drmanac et al. | C12Q 1/6874 435/5 |
| 2007/0231817 A1 | 10/2007 | De Laat et al. | |
| 2008/0015494 A1 | 1/2008 | Santini, Jr. et al. | |
| 2008/0125328 A1* | 5/2008 | Wyrick et al. | G01N 33/5308 506/17 |
| 2008/0248467 A1* | 10/2008 | Hollenbach | C12N 15/1055 435/6.11 |
| 2008/0248958 A1* | 10/2008 | Hollenbach | C12Q 1/6811 506/4 |
| 2008/0262747 A1* | 10/2008 | Kain et al. | C12Q 1/686 702/20 |
| 2009/0105959 A1* | 4/2009 | Braverman et al. | C12Q 1/68 702/19 |
| 2009/0127589 A1* | 5/2009 | Rothberg | G01N 33/5438 257/253 |
| 2009/0142758 A1* | 6/2009 | van Eijk | C12Q 1/6827 435/6.11 |
| 2009/0143240 A1* | 6/2009 | Harbison et al. | C12Q 1/6837 436/501 |
| 2009/0186352 A1* | 7/2009 | Akoulitchev et al. | C12Q 1/6883 435/6.14 |
| 2009/0191598 A1* | 7/2009 | Ruan et al. | C12Q 1/6806 435/91.52 |
| 2009/0221428 A1* | 9/2009 | Young | C12Q 1/6809 506/4 |
| 2009/0292665 A1* | 11/2009 | Den Hartog | G16B 30/00 706/48 |
| 2010/0029925 A1* | 2/2010 | Brevnov | C12N 15/1013 536/25.41 |
| 2010/0068775 A1* | 3/2010 | Achkar et al. | C12P 7/22 435/156 |
| 2010/0075861 A1 | 3/2010 | De Laat et al. | |
| 2010/0105052 A1* | 4/2010 | Drmanac | C12Q 1/6874 435/6.12 |
| 2010/0120036 A1* | 5/2010 | Shiota | C12Q 1/683 435/6.12 |
| 2010/0143414 A1* | 6/2010 | Nahm | A61P 11/00 424/244.1 |
| 2010/0150965 A1* | 6/2010 | Kopecko et al. | C07K 16/1278 424/246.1 |
| 2010/0167954 A1* | 7/2010 | Earnshaw et al. | C12Q 1/6855 506/17 |
| 2012/0014977 A1* | 1/2012 | Furihata | C07K 14/4748 424/185.1 |
| 2012/0165219 A1* | 6/2012 | Van Der Zaag | C12Q 1/6834 506/9 |
| 2012/0252012 A1* | 10/2012 | Armougom | C12Q 1/689 435/6.11 |
| 2012/0253689 A1* | 10/2012 | Rogan | G16B 30/00 702/20 |
| 2018/0057868 A1* | 3/2018 | Walder | C12Q 1/6869 |

FOREIGN PATENT DOCUMENTS

| | | |
|---|---|---|
| EP | 0185444 A2 | 6/1986 |
| EP | 2354243 | 8/2011 |
| JP | 62026300 | 2/1987 |
| JP | 2003038190 A | 2/2003 |
| JP | 2009500031 A | 1/2009 |
| JP | 2010515449 A | 5/2010 |
| JP | 2013530709 A | 8/2013 |
| WO | WO 03/031647 A1 * | 4/2003 ............ C12Q 1/68 |
| WO | WO-03031647 A1 * | 4/2003 ............ G16B 20/00 |
| WO | WO 2007/004057 A2 | 1/2007 |
| WO | WO 2008/008845 A2 | 1/2008 |
| WO | 2008084405 | 7/2008 |
| WO | 2008084405 A2 | 7/2008 |
| WO | 2009053039 A1 | 4/2009 |
| WO | WO 2012/005595 | 1/2012 |

OTHER PUBLICATIONS

Dostie et al, Chromosome Conformation Capture Carbon Copy (5C): A massively parallel solution for mapping interactions between genomic elements, 2006, 16, 1299-1309 (Year: 2006).*

De Vree et al, Targeted sequencing by proximity ligation for comprehensive variant detection and local haplotyping, 2014, Nature Biotecnology, 32, 1020-1025 (Year: 2014).*

"Viruses" (Wikipedia.com, accessed Nov. 24, 2012).*

"How many species of bacteria are there" (wisegeek.com; accessed Jan. 21, 2014).*

"Fungi," (Wikipedia.com; accessed Jun. 3, 2013).*

"Plant," (Wikipedia.com; accessed Mar. 8, 2013).*

"Mammal," (Wikipedia.com; accessed Sep. 22, 2011).*

"Murinae," (Wikipedia.com, accessed Mar. 18, 2013).*

"Human genome", Wikipedia.com (accessed Sep. 20, 2016).*

"List of sequenced bacterial genomes" (Wikipedia.com; accessed Jan. 24, 2014).*

"Viruses", Wikipedia.com, accessed Nov. 24, 2012. (Year: 2012).*

"How many species of bacteria are there", wisegeek.com; accessed Jan. 21, 2014. (Year: 2014).*

"Fungi," Wikipedia.com; accessed Jun. 3, 2013. (Year: 2013).*

"Plant," Wikipedia.com; accessed Mar. 8, 2013. (Year: 2013).*

"Mammal," Wikipedia.com; accessed Sep. 22, 2011. (Year: 2011).*

"Murinae," Wikipedia.com, accessed Mar. 18, 2013. (Year: 2013).*

"Human genome", Wikipedia.com; accessed Sep. 20, 2016. (Year: 2016).*

"List of sequenced bacterial genomes", Wikipedia.com; accessed Jan. 24, 2014. (Year: 2014).*

Zhang et al., Bioinformatics, vol. 19, No. 1, 2003, pp. 14-21. (Year: 2003).*

Sommer and Tautz, "Minimal homology requirements for PCR primers", Nucleic Acids Research, vol. 17, No. 16, 1989, p. 6749. (Year: 1989).*

Langowski, "Chromosome conformation by crosslinking", Nucleus, 1:1, pp. 37-39. (Year: 2010).*

Langowski, "Chromosome conformation by crosslinking", Nucleus, 1:1, Jan.-Feb. 2010, pp. 37-39. (Year: 2010).*

"Human Genome", Wikipedia.com, accessed Aug. 4, 2021. (Year: 2021).*

Human Genome, Wikiedia.com, accessed Aug. 4, 2021. (Year: 2021).*

"Human genome", Wikipedia.com, pp. 1-16, accessed Aug. 4, 2021. (Year: 2021).*

"New COVID-19 Variants", CDC.gov, pp. 1-3, accessed Jan. 21, 2021. (Year: 2021).*

First Notification of Office Action dated Dec. 23, 2013, in CN Patent Application No. 201180034117.6.

Splinter et al., 3C Technology Analyzing the Spatial Organization of Genomic loci In Vivo, Methods in Enzymology, Jan. 1, 2004, pp. 493-507, vol. 375, Academic Press Inc., San Diego, CA, US.

Simonis et al., FISH-eyed and genomic-wide views on the spatial organization of gene expression, Biochemica et Biophysica Acta. Molecular Cell Research, Nov. 1, 2008, pp. 2052-2060, vol. 1783, No. 11, Elsevier Science Publishers, Amsterdam, NL.

De Laat et al., Inter-chromosomal gene regulation in the mammalian cell nucleus, Current Opinion in Genetics & Development, Oct. 1, 2007, pp. 456-464, vol. 17, No. 5, Current Biology Ltd.

(56) References Cited

OTHER PUBLICATIONS

PCT International Search Report, PCT/NL2011/050504, dated Jan. 23, 2012.
Brownstein et al., High-throughput sequencing to decipher the genetic heterogeneity of deafness, Genome Biology, 2012, 13:245.
Churko et al., Overview of High Throughput Sequencing Technologies to Elucidate Molecular Pathways in Cardiovascular Diseases, Circ Res. 2013, pp. 1613-1623, vol. 112.
Fouhy et al., High-Throughput Sequencing Reveals the Incomplete, Short-Term Recovery of Infant Gut Microbiota following Parenteral Antibotic Treatment with Ampicillin and Gentamicin, Antimicrobial Agents and Chemotherapy, Nov. 2012, pp. 5811-5820, vol. 56, No. 11.
Illumina introduction to Next-Generation Sequencing Technology, at least as early as 2011, 12 pages.
McAdam et al., High-throughput sequencing for the study of bacterial pathogen biology, Science Direct, 2014, pp. 106-113, vol. 19.
King et al., A Dictionary of Genetics, Fifth Edition, 1997, p. 80.
Mamanova et al., Target-Enrichment Strategies For Next-Generation Sequencing, Nature Methods, Feb. 2010, pp. 111-118.
Examination Report for EPO application 11 736 190.7 dated Jul. 21, 2015.
Japanese Notice of Reasons for Rejection for Japanese patent application P2013-518301 dated Aug. 11, 2015.
De Vree et al., Targeted sequencing by proximity ligation for comprehensive variant detection and local haplotyping, Nature Biotechnology, Oct. 2014, pp. 1019-1025, vol. 32, No. 10.
Spinella, Dominic, "Tandem Arrayed Ligation of Expressed Sequence Tags (Talest): a New Method for Generating Global Gene Expression Profiles", Nucleic Acids Research, Jun. 25, 1999, 8 pgs.
Gnirke, Andreas, "Solution Hybrid Selection with Ultra-Long Oligonucleotides for Massively Parallel Targeted Sequencing", Nature Biotechnology, Feb. 2009, 8 pgs.
Glisin, et al. "The Cross-Linking of DNA by Ultraviolet Radiation." BBA Section Nucleic Acids and Protein Synthesis. 142.2 (1967): 314-322.
Nejedly et al. "Crosslinking of the Complementary Strands of DNA by UV Light: Dependence on the Oligonucleotide Composition of the UV Irradiated DNA." BBA—Gene Structure and Expression, vol. 1517, No. 3, 2001, pp. 365-375.
Lieberman-Aiden, Erez, et al. "Comprehensive Mapping of Long-Range Interactions Reveals Folding Principles of the Human Genome. (Reports)(Author Abstract)(Report)." Science, vol. 326, No. 5950, 2009, pp. 289-293.

* cited by examiner

3-D GENOMIC REGION OF INTEREST SEQUENCING STRATEGIES

CROSS-REFERENCE TO RELATED APPLICATIONS

This application is the national stage entry of PCT International Application PCT/NL2011/050504, filed on Jul. 8, 2011, designating the United States of America, and published in English as WO 2012/005595 A2, which claims priority under Article 8 of the Patent Cooperation Treaty and benefit under 35 U.S.C. § 119(e) to USSN 61/362,778, filed on Jul. 9, 2010.

FIELD OF THE INVENTION

The present invention relates to the field of molecular biology and more in particular to DNA technology. The invention in more detail relates to the sequencing of DNA. The invention relates to strategies for determining (part of) a DNA sequence of a genomic region of interest. In particular the invention relates to the determination of the sequence of parts of a genome that are in a spatial configuration with each other. The invention further relates to uses of the methods of the invention in the development of personalised diagnostics and medical treatment, in the screening of tissues for the presence of malignancies and other conditions.

BACKGROUND

Considerable effort has been devoted to develop "target enrichment" strategies for sequencing, in which genomic regions from a DNA sample are selectively captured and/or selectively amplified and subsequently sequenced (reviewed in Mamanova et al., Nature Methods, 2010, (2):111-118). Genomic enrichment strategies are important, as they allow to focus on a particular genomic region, which, as compared to complete genome analysis, is more time and cost effective, and also much less difficult to analyze. Different genomic enrichment strategies exist. For instance, performing a PCR reaction, using a single primer pair, will amplify a genomic region, and thus enrich for that genomic region. However, the size of PCR product that can be made is limited. Long PCR protocols currently have an upper limit of 10-40 kB which can be amplified (Cheng et al., Proc Natl Acad Sci USA, 1994; 91(12): 5695-5699), but these approaches tend to lack robustness and each PCR requires optimization and validation, and still, the size limit is limited. In order to increase the size of regions that can be amplified, as well as the robustness of the assay, tiled approaches have been developed using a multitude of PCR primer pairs designed specifically for a genomic region of interest. These primers are used for example in a multiplex PCR approach or a Rain Dance PCR. Various enzymatic methods, such as target circularization, are compatible with such targeted amplification strategies. Other methods involve the use of capture probes, on an array or in solution, wherein probes of 60-120 bases in length are used to capture the genomic region of interest via hybridisation.

As is clear from the examples above, in order to enrich a genomic region of interest, sequence information throughout the genomic region of interest is required beforehand, because this is needed to design probes and/or primers to capture and/or amplify the genomic region of interest. For instance, to enrich a 30 Mb sequence, 6,000 separate PCRs would typically be required. With capture probes, even more sequence information is required, as at least as many as 250.000 120 bp probes would be required and have to be designed to capture a 30 Mb sequence. These assays are biased by using sequence data for the probes and/or primers which largely cover the genomic region of interest. They do not pick up sequences that deviate too much from the designed template sequences and will therefore for instance not detect insertions. In addition, these approaches require fragmenting DNA into, typically, sequences of a few 100 basepairs before the analysis. This means that the genomic region of interest is broken up into many pieces, resulting in loss of information, a.o. regarding rearrangements within the region of interest. Hence, there is a need for improved genomic enrichment strategies which are much less biased, which do not require thousands of short sequences, and, which enable hypothesis neutral complete sequencing of the region of interest.

In the study of the mammalian nuclear architecture, chromosome conformation capture (3C/4C) assays have been developed, with which the structural organisation of a genomic region can be analysed (WO 2007/004057, WO 2008/08845). These technologies, involve the in vivo crosslinking of cells, e.g. with formaldehyde, such that the chromatin architecture including the DNA is fixed in its three dimensional architecture. Next, the chromatin is fragmented, e.g. with a restriction enzyme, followed by ligation of the crosslinked DNA fragments. The result is that DNA fragments that are in proximity of each other are ligated. The ligation products are subsequently PCR amplified and analysed for the interaction frequency of ligated DNA fragments, which is indicative of the proximity of fragments. The PCR amplification can be based on a target sequence within the genomic region of interest. A high frequency of interaction with the genomic region of interest indicates a close proximity, a low frequency of interaction indicates a distant proximity. In order to identify the DNA fragments, sequence information is required. Such sequence information can be provided by detecting amplified fragments with a microarray, comprising probes, or by sequencing a small part of amplified fragments (typically, a minimum of 20 to 30 basepairs is sufficient to identify the corresponding position on a genome). In any case, the number of DNA fragments identified, i.e. the frequency of interaction, indicates the proximity of the fragment to the viewpoint, which information may be used to determine intrachromosomal and interchromosomal interactions.

SUMMARY OF THE INVENTION

It was now found that the procedure of crosslinking and fragmenting DNA within a cell, and subsequent ligation of cross-linked DNA fragments, may provide an ideal starting point for analysing a genomic region of interest comprising a target nucleotide sequence, i.e. the linear chromosome template surrounding a target nucleotide sequence. The invention is based on the concept that crosslinking of DNA will preferentially crosslink those sequences that are close on the linear chromosome template to a target nucleotide sequence. Formaldehyde, for instance, may be used as a crosslinker. After crosslinking, the DNA can be subjected to (enzymatic) treatments, i.e. fragmenting and ligation, while the DNA remains in its crosslinked state. Only crosslinked fragments which are in the proximity of each other may be ligated. DNA fragments that ligate to the DNA fragment comprising the target nucleotide sequence are in fact representative of the genomic region of interest comprising the target nucleotide sequence. This is because the chance of intra-chromosomal crosslinking is on average always higher than interchromosomal crosslinking frequencies. In general, the chance of different fragments being crosslinked correlates inversely with the linear distance. As an estimate, and depending on the actual crosslinking conditions, 20-30% of the fragments ligated with a target nucleotide of interest locate within 0.5 Mb from the target nucleotide sequence, while 50-80% of the fragments ligated with a target nucleotide of interest originate from the chromosome comprising the target nucleotide sequence. The ligated DNA fragments comprising the target nucleotide sequence, and thus the genomic region of interest, may be amplified, i.e. enriched, by using one or more oligonucleotide primer that recognize the target nucleotide sequence. The sequence of the genomic region of interest can subsequently be determined using (high throughput) sequencing technologies well known in the art. The method is little biased, as no extensive sequence information is required to focus on the genomic region of interest. For instance, a genomic region of interest may comprise an allele of interest. A target nucleotide sequence may be selected such that it is not within the sequence of the allele of interest. A genomic region of interest may then be amplified by using a target nucleotide sequence, without requiring sequence information of the allele of interest. Thus, the allele of interest may be enriched for, without requiring any sequence from that allele. The effect is that the method of enrichment is not biased by using oligonucleotides and/or probes which cover the allelic sequence of interest. In addition, as the ligation step involves the ligation of fragments that are in proximity of each other, the method may also allow for the sequence analysis of separate alleles. For instance, when a crosslinked DNA sample comprises multiple alleles (e.g. because the DNA sample originates from a heterogeneous cell population, or because the ploidy is greater than one), each allele may have a different genomic neighbourhood. A DNA fragment, comprising a target nucleotide sequence, will only interact with DNA fragments that are in the same space. fragments that are in the same space. Thus ligated DNA fragments are representative of the genomic environment from which the fragments originate. By determining at least part of the sequence of all the different ligated DNA fragments, DNA fragment sequences may subsequently be coupled using the sequence information of the different ligated DNA fragments and a sequence for separate genomic regions of interest may be built.

DEFINITIONS

In the following description and examples, a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

A "genomic region of interest" according to the invention is a DNA sequence of an organism of which it is desirable to determine, at least part of, the DNA sequence. For instance, a genomic region which is suspected of comprising an allele associated with a disease may be a genomic region of interest. As used herein, the term "allele(s)" means any of one or more alternative forms of a gene at a particular locus. In a diploid cell of an organism, alleles of a given gene are located at a specific location, or locus (loci plural) on a chromosome. One allele is present on each chromosome of the pair of homologous chromosomes. Thus, in a diploid cell, two alleles and thus two separate (different) genomic regions of interest may exist.

A "nucleic acid" according to the present invention may include any polymer or oligomer of pyrimidine and purine bases, preferably cytosine, thymine, and uracil, and adenine and guanine, respectively (See Albert L. Lehninger, Principles of Biochemistry, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

A "sample DNA" is a sample that is obtained from an organism or from a tissue of an organism, or from tissue and/or cell culture, which comprises DNA. A sample DNA from an organism may be obtained from any type of organism, e.g. micro-organisms, viruses, plants, fungi, animals, humans and bacteria, or combinations thereof. For example, a tissue sample from a human patient suspected of a bacterial and/or viral infection may comprise human cells, but also viruses and/or bacteria. The sample may comprise cells and/or cell nuclei. The sample DNA may be from a patient or a person which may be at risk or suspected of having a particular disease, for example cancer or any other condition which warrants the investigation of the DNA of the organism.

With "crosslinking" according to the invention is meant reacting DNA at two different positions, such that these two different positions may be connected. The connection between the two different positions may be directly, forming a covalent bond between DNA strands. Two DNA strands may be crosslinked directly using UV-irradiation, forming covalent bonds directly between DNA strands. The connection between the two different positions may be indirectly, via an agent, e.g. a crosslinker molecule. A first DNA section may be connected to a first reactive group of a crosslinker molecule comprising two reactive groups, that second reactive group of the crosslinker molecule may be connected to a second DNA section, thereby crosslinking the first and second DNA section indirectly via the crosslinker molecule. A crosslink may also be formed indirectly between two DNA strands via more than one molecule. For example, a typical crosslinker molecule that may be used is formaldehyde. Formaldehyde induces protein-protein and DNA-protein crosslinks. Formaldehyde thus may crosslink different DNA strands to each other via their associated proteins. For example, formaldehyde can react with a protein and DNA, connecting a protein and DNA via the crosslinker molecule. Hence, two DNA sections may be crosslinked using formaldehyde forming a connection between a first DNA section and a protein, the protein may form a may form a second connection with another formaldehyde molecule that connects to a second DNA section, thus forming a crosslink which may be depicted as DNA1-crosslinker-protein-crosslinker-DNA2. In any case, it is understood that crosslinking according to the invention involves forming connections (directly or indirectly) between strands of DNA that are in physical proximity of each other. DNA strands may be in physical proximity of each other in the cell, as DNA is highly organised, while being separated from a sequence point of view e.g. by 100 kb. As long as the crosslinking method is compatible with subsequent fragmenting and ligation steps, such crosslinking may be contemplated for the purpose of the invention.

A "sample of crosslinked DNA" is a sample DNA which has been subjected to crosslinking. Crosslinking the sample DNA has the effect that the three-dimensional state of the DNA within the sample remains largely intact. This way, DNA strands that are in physical proximity of each other remain in each others vicinity.

"Reversing crosslinking" according to the invention comprises breaking the crosslinks such that the DNA that has been crosslinked is no longer crosslinked and is suitable for subsequent amplification and/or sequencing steps. For example, performing a protease K treatment on a sample DNA that has been crosslinked with formaldehyde will digest the protein present in the sample. Because the crosslinked DNA is connected indirectly via protein, the protease treatment in itself may reverse the crosslinking between the DNA. However, the protein fragments that remain connected to the DNA may hamper subsequent sequencing and/or amplification. Hence, reversing the connections between the DNA and the protein may also result in "reversing crosslinking". The DNA-crosslinker-protein connection may be reversed through a heating step for example by incubating at 70° C. As in a sample DNA large amounts of protein is present, it is often desirable to digest the protein with a protease in addition. Hence, any "reversing crosslinking" method may be contemplated wherein the DNA strands that are connected in a crosslinked sample becomes suitable for sequencing and/or amplification.

"Fragmenting DNA" includes any technique that, when applied to DNA, which may be crosslinked DNA or not, or any other DNA, results in DNA fragments. Techniques well known in the art are sonication, shearing and/or enzymatic restriction, but other techniques can also be envisaged.

A "restriction endonuclease" or "restriction enzyme" is an enzyme that recognizes a specific nucleotide sequence (recognition site) in a double-stranded DNA molecule, and will cleave both strands of the DNA molecule at or near every recognition site, leaving a blunt or a 3'- or 5'-overhanging end. The specific nucleotide sequence which is recognized may determine the frequency of cleaving, e.g. a nucleotide sequence of 6 nucleotides occurs on average every 4096 nucleotides, whereas a nucleotide sequence of 4 nucleotides occurs much more frequently, on average every 256 nucleotides.

"Ligating" according to the invention involves the joining of separate DNA fragments. The DNA fragments may be blunt ended, or may have compatible overhangs (sticky overhangs) such that the overhangs can hybridise with each other. The joining of the DNA fragments may be enzymatic, with a ligase enzyme, DNA ligase. However, a non-enzymatic ligation may also be used, as long as DNA fragments are joined, i.e. forming a covalent bond. Typically a phosphodiester bond between the hydroxyl and phosphate group of the separate strands is formed.

"Oligonucleotide primers", in general, refer to strands of nucleotides which can prime the synthesis of DNA. DNA polymerase cannot synthesize DNA de novo without primers. A primer hybridises to the DNA, i.e. base pairs are formed. Nucleotides that can form base pairs, that are complementary to one another, are e.g. cytosine and guanine, thymine and adenine, adenine and uracil, guanine and uracil. The complementarity between the primer and the existing DNA strand does not have to be 100%, i.e. not all bases of a primer need to base pair with the existing DNA strand. From the 3'-end of a primer hybridised with the existing DNA strand, nucleotides are incorporated using the existing strand as a template (template directed DNA synthesis). We may refer to the synthetic oligonucleotide molecules which are used in an amplification reaction as "primers".

"Amplifying" refers to a polynucleotide amplification reaction, namely, a population of polynucleotides that are replicated from one or more starting sequences. Amplifying may refer to a variety of amplification reactions, including but not limited to polymerase chain reaction (PCR), linear polymerase reactions, nucleic acid sequence-based amplification, rolling circle amplification and like reactions.

"Sequencing" refers to determining the order of nucleotides (base sequences) in a nucleic acid sample, e.g. DNA or RNA. Many techniques are available such as Sanger sequencing and High throughput sequencing technologies such as offered by Roche, Illumina and Applied Biosystems.

The term "contig" is used in connection with DNA sequence analysis, and refers to reassembled contiguous stretches of DNA derived from two or more DNA fragments having contiguous nucleotide sequences. Thus, a contig may be a set of overlapping DNA fragments that provides a (partial) contiguous sequence of a genomic region of interest. A contig may also be a set of DNA fragments that, when aligned to a reference sequence, may form a contiguous nucleotide sequence. For example, the term "contig" encompasses a series of (ligated) DNA fragment(s) which are ordered in such a way as to have sequence overlap of each (ligated) DNA fragment(s) with at least one of its neighbours. The linked or coupled (ligated) DNA fragment(s), may be ordered either manually or, preferably, using appropriate computer programs such as FPC, PHRAP, CAP3 etc, and may also be grouped into separate contigs.

An "adaptor" is a short double-stranded oligonucleotide molecule with a limited number of base pairs, e.g. about 10 to about 30 base pairs in length, which are designed such that they can be ligated to the ends of fragments. Adaptors are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adaptor molecule may be designed such that it is compatible with the end of a restriction fragment and can be ligated thereto; the other end of the adaptor can be designed so that it cannot be ligated, but this does need not to be the case, for instance when an adaptor is to be ligated in between DNA fragments.

An "identifier" is a short sequence that can be added to an adaptor or a primer or included in its sequence or otherwise used as label to provide a unique identifier. Such a sequence identifier (or tag) can be a unique base sequence of varying but defined length, typically from 4-16 bp used for identifying a specific nucleic acid sample. For instance 4 bp tags allow 4(exp4)=256 different tags. Typical examples are ZIP sequences, known in the art as commonly used tags for unique detection by hybridization (Iannone et al. Cytometry 39:131-140, 2000). Identifiers are useful according to the invention, as by using such an identifier, the origin of a (PCR) sample can be determined upon further processing. In the case of combining processed products originating from different nucleic acid samples, the different nucleic acid samples may be identified using different identifiers. For instance, as according to the invention sequencing may be performed using high throughput sequencing, multiple samples may be combined. Identifiers may then assist in identifying the sequences corresponding to the different samples. Identifiers may also be included in adaptors for ligation to DNA fragments assisting in DNA fragment sequences identification. Identifiers preferably differ from each other by at least two base pairs and preferably do not contain two identical consecutive bases to prevent misreads. The identifier function can sometimes be combined with other functionalities such as adaptors or primers.

"Size selection' according to the invention involves techniques with which particular size ranges of molecules, e.g. (ligated) DNA fragments or amplified (ligated) DNA fragments, are selected. Techniques that can be used are for instance gel electrophoresis, size exclusion, gel extraction chromatography, but are not limited thereto, as long as molecules with a particular size can be selected, such a technique will suffice.

With the term "aligning" and "alignment" is meant the comparison of two or more nucleotide sequence based on the presence of short or long stretches of identical or similar nucleotides. Methods and computer programs for alignment are well known in the art. One computer program which may be used or adapted for aligning is "Align 2", authored by Genentech, Inc., which was filed with user documentation in the United States Copyright Office, Washington, D.C. 20559, on Dec. 10, 1991.

FIGURES

FIG. 1 shows a schematic of a method for determining the sequence of a genomic region of interest according to the invention. The method involves:
(a) crosslinking, wherein e.g. formaldehyde fixation cross-links spatially nearby DNA sequences in the nucleus (N) (often being sequences close on the chromosome (Ch), e.g. sequences of the same gene) via their associated proteins (e.g. histones). 5 hypothetical fragments of a genomic region of interest A, B, C, D and E are indicated;
(b) next, the crosslinked sample DNA is fragmented, e.g. by performing a digestion with a restriction enzyme (e.g. a frequent (four) cutter (e.g NIaIII);
(c) cross-linked restriction fragments are ligated to form DNA circles;
(d) after reversing the crosslinking an amplification step, e.g. PCR, is performed with an (inverse) PCR primerset for a viewpoint close to or within the genomic region of interest. Fragments (A, B, C, D and E) crosslinked to this viewpoint are amplified and enriched over the remainder of the genome.
The amplified fragments are sequenced, e.g. by sequencing across entire circles (long reads), PCR amplified material may also be first fragmented to create a sequencing library compatible e.g. for Illumina or SOLiD sequencing.
(e) next a contig is built from the reads, the sequences may be compared to a reference genome to identify genetic variation.

Figure 2:
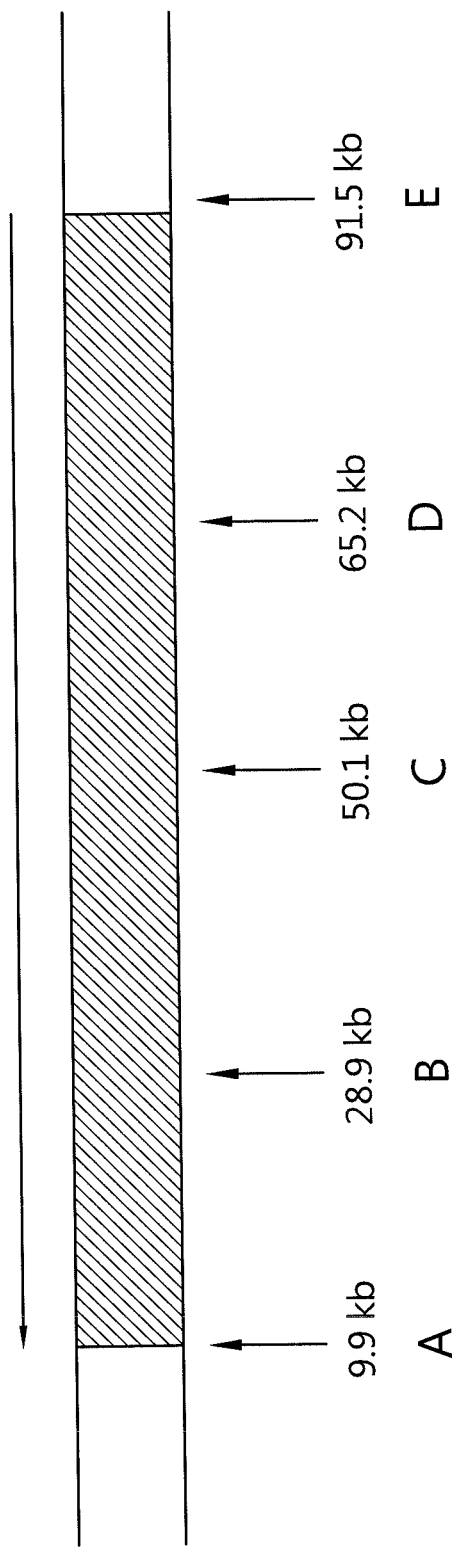

FIG. 2 shows a scheme of the BRCA1 gene with 5 different viewpoints (A, B, C, D and E). The black arrow indicates the sense direction. The numbers in the circles with the arrows indicate the position on the gene sequence. Viewpoint E is at the start of the gene and viewpoint A at the end. The viewpoints are separated by approximately 15-25 kB.

Figure 3A:
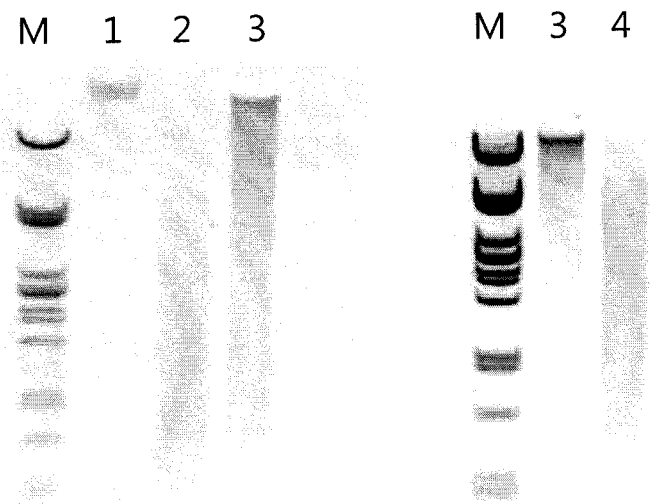
Figure 3B:
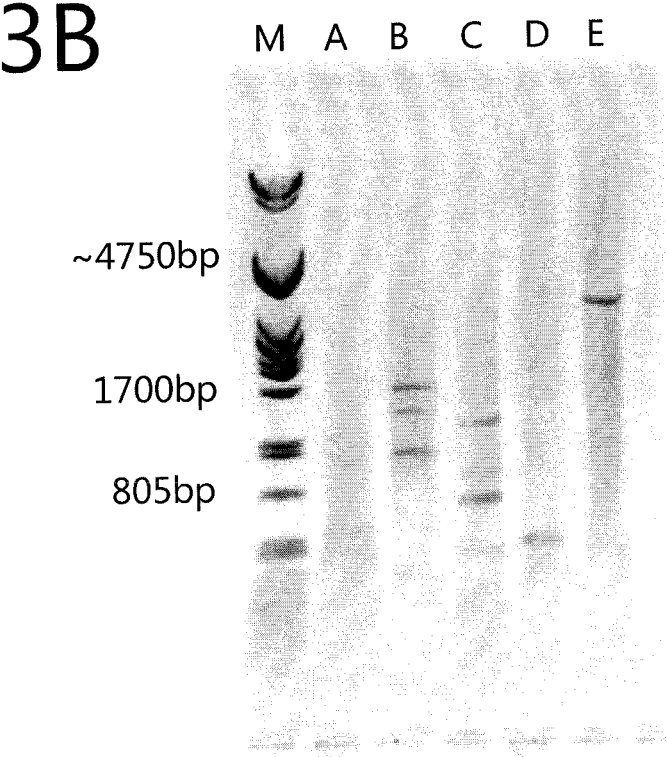

FIG. 3 Gel electrophoresis of DNA samples is shown taken during the preparation of a crosslinked sample DNA for the sequencing of the BRCA1 gene as described in the examples.
(A) Lane M indicates a lambda DNA Pstl marker DNA, lane 1 shows an undigested control, lane 2 shows a NIaIII first digested control, lane 3 is a ligation control after the ligation of NIaIII first digested sample lane 4 shows a second digestion with Nspl.
(B) Lane M shows a lambda DNA Pstl marker. Lanes A, B, C, D and E shows the amplification products of the different DNA amplifications, corresponding to samples from step 67 as described in the example section, and corresponding to the viewpoints described in FIG. 2.

DETAILED DESCRIPTION OF THE INVENTION

According to one aspect of the invention, a method is provided for determining the sequence of a genomic region of interest comprising a target nucleotide sequence, comprising fragmenting a crosslinked DNA, ligating the fragmented crosslinked DNA, reversing the crosslinking and determining at least part of the sequences of ligated DNA fragments which comprise a target nucleotide sequence, and using the determined sequences to build a sequence of the genomic region of interest.

A sample of crosslinked DNA comprises a sample DNA which has been subjected to crosslinking. Crosslinking the sample DNA as it is present in the sample results in largely maintaining the three dimensional architecture of the DNA. For example, a standard crosslinking agent that may be used is formaldehyde. Samples may be taken from a patient and/or from diseases tissue, and may also be derived from other organisms or from separate sections of the same organism, such as samples from one patient, one sample from healthy tissue and one sample from diseased tissue. Samples may thus be analysed according to the invention and compared with a reference sample, or different samples may be analysed and compared with each other. For example, from a patient being suspected of having breast cancer, a biopsy may be obtained from the suspected tumour. Another biopsy may be obtained from non-diseased tissue. From both tissue biopsies may be analysed according to the invention. Genomic regions of interests may be the BRCA1 and BRCA2 gene, which genes are 83 and 86 kb long (reviewed in Mazoyer, 2005, Human Mutation 25:415-422). By determining the genomic region of interest sequence according to the invention and comparing the genomic region sequences of the different biopsies with each other and/or with a reference BRCA gene sequence, genetic mutations may be found that will assist in diagnosing the patient and/or determining treatment of the patient and/or predicting prognosis of disease progression.

By fragmenting a sample of crosslinked DNA, the DNA fragments that originate from a genomic region of interest remain in proximity of each other because they are crosslinked. When these crosslinked DNA fragments are subsequently ligated, DNA fragments of the genomic region of interest, which are in the proximity of each other due to the crosslinks, are ligated. This type of ligation may also be referred to as proximity ligation. DNA fragments comprising the target nucleotide sequence may ligate with DNA fragments within a large linear distance on sequence level. By determining (at least part of) the sequence of ligated fragments that comprise the fragment comprising the target nucleotide sequence, sequences of DNA fragments within the spatial surrounding of the genomic region of interest are are obtained. Each individual target nucleotide sequence is likely to be crosslinked to multiple other DNA fragments. As a consequence, often more than one DNA fragment may be ligated to a fragment comprising the target nucleotide sequence. By combining (partial) sequences of the (amplified) ligated DNA fragments that were ligated with a fragment comprising the target nucleotide sequence, a sequence of the genomic region of interest may be built. A DNA fragment ligated with the fragment comprising the target nucleotide sequence includes any fragment which may be present in ligated DNA fragments.

Methods are known in the art that involve crosslinking DNA, as well as fragmenting and ligating the DNA fragments (e.g. WO 2007/004057 or WO 2008/08845). Such methods are aimed at identifying interaction frequencies between different DNA fragments, not at identifying the primary nucleotide sequence of fragments neighbouring a target nucleotide sequence. The original idea of using 4C for the detection of interaction frequencies only required a short sequence read. The frequency of the interacting short sequence reads are plotted against chromosomal positions of the reads. The pattern of such a plot is indicative for whether a particular genomic region of interest may interact with a region on elsewhere in the genome, or that, e.g. translocations between chromosomes have occurred. For instance, in case a high frequency of reads is observed on a chromosome other than the one containing the target nucleotide sequence it is indicative of a translocation. In the current invention, the frequency of interaction is not determined. In the current invention it was now realised that by fragmenting crosslinked DNA and subsequently ligating the DNA fragments, in fact a genomic region surrounding the target nucleotide sequence is captured, that when sequenced, allows reconstructing contigs of the genomic region. Whereas in the methods known in the art, the focus has been on determining the frequency of interaction of short sequence reads with a target nucleotide sequence, the focus of the current invention is on determining the complete, or at least a large part of, the sequence of ligated DNA fragments (comprising the DNA fragment with the target nucleotide) such that from the sequences of DNA fragments and coupling of ligated DNA fragments, contigs may be built for a genomic region of interest.

Linearized Ligated Fragments

In one embodiment of the invention, a method is provided for determining the sequence of a genomic region of interest comprising a target nucleotide sequence, comprising the steps of:
a) providing a sample of crosslinked DNA;
b) fragmenting the crosslinked DNA;
c) ligating the fragmented crosslinked DNA;
d) reversing the crosslinking;
e) optionally fragmenting the DNA of step d), preferably with a restriction enzyme
f) optionally, ligating the fragmented DNA of step d) or e) to at least one adaptor;
g) optionally, amplifying DNA of step d) or e) comprising the target nucleotide sequence using at least one oligonucleotide primer which hybridises to the target nucleotide sequence, or amplifying DNA of step f) using at least one additional primer which hybridises to the at least one adaptor;
h) determining at least part of the sequence of the (amplified) ligated DNA fragments of step d), e), f) or g) comprising the target nucleotide sequence preferably using high throughput sequencing;
i) building a contig of the genomic region of interest from the determined sequences.

In step a) a sample of crosslinked DNA is provided as outlined herein elsewhere. The sample of crosslinked DNA is fragmented in step b). By fragmenting the crosslinked DNA, DNA fragments are produced which are held together by the crosslinks. The fragmenting step b) may comprise sonication, and may be followed by enzymatic DNA end repair. Sonication results in the fragmenting of DNA at random sites, which can be either blunt ended, or can have 3'- or 5'-overhangs, as these DNA breakage points occur randomly, the DNA may be repaired (enzymatically), filling in possible 3'- or 5'-overhangs, such that DNA fragments are obtained which have blunt ends that allow ligation of the fragments to adaptors and/or to each other in the subsequent step c). Alternatively, the overhangs may also be made blunt ended by removing overhanging nucleotides, using e.g. exonucleases. The fragmenting step b) may also comprise fragmenting with one or more restriction enzymes, or combinations thereof. Fragmenting with a restriction enzyme is advantageous as it may allow control of the average fragment size. The fragments that are formed may have compatible overhangs or blunt ends that allow ligation of the fragments in the subsequent step c). Furthermore, when dividing a sample of cross-linked DNA into a plurality of subsamples, for each subsample restriction enzymes with different recognition sites may be used. This is advantageous because by using different restriction enzymes having different recognition sites, different DNA fragments can be obtained from each subsample.

In the next step c), the fragments are ligated. Since a fragment comprising a target nucleotide sequence may be crosslinked to multiple other DNA fragments, more than one DNA fragment may be ligated to the fragment comprising the target nucleotide sequence. This may result in combinations of DNA fragments which are in proximity of each other as they are held together by the cross links. Different combinations and/or order of the DNA fragments in ligated DNA fragments may be formed. In case the DNA fragments are obtained via enzymatic restriction, the recognition site of the restriction enzyme is known, which makes it possible to identify the fragments as remains of or reconstituted restriction enzyme recognition sites may indicate the separation between different DNA fragments. In case the DNA fragments were obtained via random fragmentation, such as sonication and subsequent enzymatic DNA end repair, it may be more difficult to distinguish one fragment from another. Irrespective of what fragmenting method is used, the ligation step c) may be performed in the presence of an adaptor, ligating adaptor sequences in between fragments. Alternatively the adaptor may be ligated in a separate step. This is advantageous because the different fragments can be easily identified by identifying the adaptor sequences which are located in between the fragments. For example, in case DNA fragment ends were blunt ended, the adaptor sequence would be adjacent to each of the DNA fragment ends, indicating the boundary between separate DNA fragments. Next, the crosslinking is reversed in step d), which results in a pool of ligated DNA fragments that comprise two or more fragments. A subpopulation of the pool of ligated DNA fragments comprises a DNA fragment which comprises the target nucleotide sequence. By reversing the crosslinking, the structural/spatial fixation of the DNA is released and the DNA sequence becomes available for subsequent steps, e.g. amplification and/or sequencing, as crosslinked DNA may not be a suitable substrate for such steps. The subsequent steps e) and/or f) may be performed after the reversal of the crosslinking, however, steps e) and/or f) may also be performed while the ligated DNA fragments are still in the crosslinked state.

The ligated DNA fragments may optionally be fragmented in step e), preferably with a restriction enzyme. The first fragmenting step and the optional second fragmenting step may be aimed at obtaining ligated DNA fragments of a size which is compatible with the subsequent amplification step and/or sequence determination step. In addition, a second fragmenting step, preferably with an enzyme may result in ligated fragment ends which are compatible with the optional ligation of an adaptor in step f). The second fragmenting step may be performed after reversing the crosslinking, however, it is also possible to perform the second fragmenting step e) and/or ligation step f) while the DNA fragments are still crosslinked.

In case the fragmenting step b) and e) comprise restriction enzymes, it is preferred that the restriction enzyme recognition site of step e) is longer than the recognition site of step b). The enzyme of e) thus cuts at a lower frequency than step b). This means that the average DNA fragment size of step b) is smaller than the average fragment size of step e) obtained after restricting DNA. This way, in the first fragmenting step, relatively small fragments are formed, which are subsequently ligated. As the second restriction enzyme of step e) cuts less frequent than step b), most of the DNA fragments may not comprise the restriction recognition site of step e). Thus, when the ligated DNA fragments are subsequently fragmented in the second step, many of the DNA fragments of step b) may remain intact. This is useful because the combined sequences of the DNA fragments of step b) may be used to build a contig for the genomic region of interest. If the fragmenting of step b) is less frequent than the fragmenting of step c), the result would be that the fragments of step b) are fragmented, which may result in the loss of relatively large DNA sequences that are useful for building a contig. Thus, irrespective of which method would be used for fragmenting in step b) and e), it is preferred that the fragmenting of step b) is more frequent as compared to step e), such that DNA fragments of step b) may largely remain intact, i.e. are largely not fragmented by step e).

To the obtained ligated DNA fragments of step d) or e) at least one adaptor is optionally ligated. The ends of the ligated DNA fragments need to be compatible with ligation of such an adaptor. As the ligated DNA fragments of step d) or e) may be linear DNA, ligation of an adaptor may provide for a primer hybridisation sequence. The adaptor sequence ligated with ligated DNA fragments comprising the target nucleotide sequence, will provide for DNA molecules which may be amplified using PCR.

In the next step g), DNA of step f) comprising the target nucleotide sequence may be amplified using at least one oligonucleotide primer which hybridises to the target nucleotide sequence, and at least one additional primer which hybridises to the at least one adaptor. As the step f) of ligating an adaptor is optional, the DNA of step d) or e) comprising the target nucleotide may also be amplified in step g) using at least one oligonucleotide primer which hybridises to the target nucleotide sequence.

Next, the sequence of the (amplified) ligated DNA fragments obtained in step d), e), f) or g) comprising the target nucleotide sequence is determined. Determining the sequence is preferably performed using high throughput sequencing technology, as this is more convenient and allows a high number of sequences to be determined to cover the complete genomic region of interest. From these determined sequences a contig may be built of the genomic region of interest. When sequences of the DNA fragments are determined, overlapping reads may be obtained from which the genomic region of interest may be built. In case the DNA fragments were obtained by random fragmentation, the random nature of the fragmentation step already may result in DNA fragments which when sequenced results in overlapping reads. By increasing the sample size, e.g. increasing the number of cells analysed, the reliability of the genomic region of interest that is built may be increased. Alternatively, when in step b) a plurality of subsamples is analysed, using different restriction enzymes, overlapping reads will also be obtained. By increasing the plurality of subsamples, the number of overlapping fragments will increase, which may increase the reliability of the contig of the genomic region of interest that is built. From these determined sequences which may overlap, a contig may be built. Alternatively, if sequences do not overlap, e.g. when a single restriction enzyme may have been used in step b), alignment of (ligated) DNA fragments with a reference sequence may allow to build a contig of the genomic region of interest.

Circularized Ligated Fragments

In an alternative embodiment, a method is provided for determining the sequence of a genomic region of interest comprising a target nucleotide sequence, comprising the steps of:
a) providing a sample of cross-linked DNA;
b) fragmenting the crosslinked DNA;
c) ligating the fragmented crosslinked DNA;
d) reversing the crosslinking;
e) optionally fragmenting the DNA of step d), preferably with a restriction enzyme
f) circularising the DNA of step d) or e);
g) optionally and preferably, amplifying the circularised DNA comprising the target nucleotide sequence using preferably at least one primer which hybridises to the target nucleotide sequence;
h) determining at least part of the sequence of the (amplified) ligated DNA fragments comprising the target nucleotide using high throughput sequencing;
i) building a contig of the genomic region of interest from the determined sequences.

In step a) a sample of crosslinked DNA is provided as outlined herein elsewhere. The sample of crosslinked DNA is fragmented in step b). By fragmenting the crosslinked DNA, DNA fragments are produced which are held together by the crosslinks. The fragmenting step b) may comprise sonication, and may be followed by enzymatic DNA end repair. Sonication results in the fragmenting of DNA at random sites, which can be either blunt ended, or can have 3'- or 5'-overhangs, as these DNA breakage points occur randomly, the DNA may be repaired (enzymatically), filling in possible 3'- or 5'-overhangs, such that DNA fragments are obtained which have blunt ends that allow ligation of the fragments to adaptors or each other in the subsequent step c). Alternatively, the overhangs may also be made blunt ended by removing overhanging nucleotides, using e.g. exonucleases. The fragmenting step b) may also comprise fragmenting with a restriction enzyme, or combinations thereof. Fragmenting with a restriction enzyme is advantageous as it allows control of the average fragment size. Furthermore, the fragments that are formed will have compatible overhangs or blunt ends that allow ligation of the fragments in the subsequent step c) without requiring further modification. Furthermore, when dividing a sample of cross-linked DNA into a plurality of subsamples, for each subsample restriction enzymes with different recognition sites may be used. This is advantageous because by using different restriction enzymes having different recognition sites, different DNA fragments can be obtained from each subsample.

In the next step c), the fragments are ligated. In case the DNA fragments were obtained via enzymatic restriction, the recognition site of the restriction enzyme is known, which makes it possible to identify the fragments as remains of or reconstituted restriction enzyme recognition sites may indicate the separation between different DNA fragments. In case the DNA fragments were obtained via random fragmentation, such as sonification and subsequent enzymatic DNA end repair, it may be more difficult to distinguish one fragment from another. Irrespective of what fragmenting method is used, the ligation step c) may be performed in the presence of an adaptor, ligating adaptor sequences in between fragments. Alternatively the adaptor may be ligated in a separate step. This is advantageous because the different fragments can be easily identified by identifying the adaptor sequences which are in between the fragments. For example, in case DNA fragment ends were blunt ended, the adaptor sequence would be adjacent to the DNA fragment ends, indicating the separate DNA fragments.

Next, the crosslinking is reversed in step d), which results in a pool of ligated DNA fragments that comprise two or more fragments. A subpopulation of the pool of ligated DNA fragments comprises a DNA fragment which comprises the target nucleotide sequence. By reversing the crosslinking, the structural/spatial fixation of the DNA is released and the DNA sequence becomes available for subsequent steps, e.g. amplification and/or sequencing, as crosslinked DNA may not be a suitable substrate for such steps. The subsequent steps e) and/or f) may be performed after the reversal of the crosslinking, however, steps e) and/or f) may also be performed while de ligated DNA fragments are still in the crosslinked state.

The ligated DNA fragments may optionally be fragmented in step e), preferably with a restriction enzyme. The fragmentation may be performed after reversing the crosslinking, but it is also envisaged that the second fragmentation is performed before crosslinking is reversed. It is preferred to use a restriction enzyme for the fragmentation, as a restriction enzyme allows control of the fragmentation step and results, if an appropriate restriction enzyme is chosen, in compatible ends of the ligated DNA fragments that are favourable for ligation of the compatible ends, resulting in circularized ligated DNA fragments, as obtained in step f). However, fragmenting using other methods, e.g. shearing and/or sonication and subsequent enzymatic DNA end repair, such that blunt ended double strand DNA is formed may also be ligated to form circularized DNA.

The first fragmenting step and the optional second fragmenting step are aimed at obtaining ligated DNA fragments which are compatible with the subsequent circularization, amplification step and/or sequence determination step. In case the fragmenting step b) and e) comprise restriction enzymes, it is preferred that the fragmenting step e) results in, on average, longer fragments as would be obtained in fragmenting step b). In case the fragmenting step b) and e) comprise restriction enzymes, it is preferred that the restriction enzyme recognition site of step e) is longer than the recognition site of step b). The enzyme of e) thus cuts at a lower frequency than step b). This means that the average DNA fragment size of step b) is smaller than the average fragment size of step e) obtained after restricting DNA. This way, in the first fragmenting step, relatively small fragments are formed, which are subsequently ligated. As the second restriction enzyme of step e) cuts less frequent than step b), most of the DNA fragments may not comprise the restriction recognition site of step e). Thus, when the ligated DNA fragments are subsequently fragmented in the second step, many of the DNA fragments of step b) may remain intact. This is useful because the combined sequences of the DNA fragments of step b) may be used to build a contig for the genomic region of interest. If the fragmenting of step b) is less frequent than the fragmenting of step c), the result would be that the fragments of step b) are fragmented, which may result in the loss of relatively large DNA sequences that are useful for building a contig. Thus, irrespective of which method would be used for fragmenting in step b) and e), it is preferred that the fragmenting of step b) is more frequent as compared to step e), such that DNA fragments of step b) may largely remain intact, i.e. are largely not fragmented by step e).

The obtained ligated DNA fragments of step d) or e), of which crosslinking has been reversed, are next circularized in step f). It may be advantageous to reverse crosslinking before the circularization, because it may be unfavourable to circularize crosslinked DNA while crosslinked. However, circularization may also be performed while the ligated DNA fragments are crosslinked. It may even be possible that an additional circularization step is not required, as during the ligation step, circularized ligated DNA fragments are already formed, and hence circularization step f) would occur simultaneously with step c). However, it is preferred to perform an additional circularization step. Circularization involves the ligation of the ends of the ligated DNA fragments such that a closed circle is formed. The circularized DNA comprising ligated DNA fragments which comprise the target nucleotide sequence, may subsequently be amplified using at least one primer which hybridises to the target nucleotide sequence. For the amplification step, reversing the crosslinking is required, as crosslinked DNA may hamper or prevent amplification. Preferably two primers are used that hybridise to the target nucleotide sequence in an inverse PCR reaction. In this way, DNA fragments of the circularized DNA, which are ligated with the DNA fragment comprising the target nucleotide sequence, may be amplified.

Next, the sequence of the (amplified) ligated DNA fragments obtained in step d), e), f) or g) comprising the target nucleotide sequence is determined. Determining the sequence is preferably performed using high throughput sequencing technology, as this is more convenient and allows a high number of sequences to be determined to cover the complete genomic region of interest. From these determined sequences, a contig may be built of the genomic region of interest. When sequences of the DNA fragments are determined, overlapping reads may be obtained from which the genomic region of interest may be built. In case the DNA fragments were obtained by random fragmentation, the random nature of the fragmentation step already may result in DNA fragments which when sequenced results in overlapping reads. By increasing the sample size, e.g. increasing the number of cells analysed, the reliability of the genomic region of interest that is built may be increased. Alternatively, when in step b) a plurality of subsamples is analysed, using different restriction enzymes, overlapping reads will also be obtained. By increasing the plurality of subsamples, the number of overlapping fragments will increase, which may increase the reliability of the contig of the genomic region of interest that is built. From these determined sequences which may overlap, a contig may be built. Alternatively, if sequences do not overlap, e.g. when a single restriction enzyme may have been used in step b), alignment of (ligated) DNA fragments with a reference sequence may allow to build a contig of the genomic region of interest.

Multiple Target Sequences

In one embodiment, a method for determining the sequence of a genomic region of interest comprising two target nucleotide sequences is provided. This method may involve the same steps as outlined above up until the amplification step. The amplification step now uses not one target nucleotide sequence, but two. For the two target nucleotide sequences, two different primers are used in a PCR reaction, one primer for each target nucleotide sequence. When the two primer binding sites from the two target nucleotide sequences are present in a ligated DNA fragment, the two primers will amplify the sequence in between the two primer binding sites provided that the primer binding sites have the right orientation. Having a circularized ligated DNA fragment may be advantageous as the chance for the two primer binding sites having the right orientation is higher as compared to a linear ligated DNA fragment (two out of four orientations will amplify, as compared to one in four for a linear ligated DNA fragment). In a further embodiment, in addition to the two target nucleotide sequences, the genomic region of interest comprises further target nucleotides, for each target nucleotide a primer is used in the PCR amplification reaction. By combining multiple target nucleotides and corresponding primers in a single amplification will increase the chance that combinations of primers will produce an amplicon.

For example, as described in the example section 5 different target nucleotides were used for the BRCA1 gene (see e.g. FIG. 2). A PCR may be performed by selecting a primer from one target nucleotide sequence (also referred to as viewpoint), e.g. A with another, B. Also, a PCR may be performed using a primer from each target nucleotide sequence, A, B, C, D and E. As these target nucleotides are in physical proximity of each other, performing such an amplification will enrich for the genomic region of interest, provided that the primer binding sites end up in ligated DNA fragments such that an amplicon can be generated.

Hence, methods are provided for determining the sequence of a genomic region of interest according to the invention, wherein the genomic region of interest comprises one or more target nucleotide sequences in addition, and wherein in the amplification step a primer is provided that hybridises with the target nucleotide sequence and one or more primers are provided for the corresponding one or more additional target nucleotides, wherein the ligated DNA fragments are amplified, or circularized DNA is amplified, using the primers.

Determining the Sequence of Ligated DNA Fragments

The step of determining the sequence of ligated DNA fragments, preferably comprises high throughput sequencing. High throughput sequencing methods are well known in the art, and in principle any method may be contemplated to be used in the invention. High throughput sequencing technologies may be performed according to the manufacturer's instructions (as e.g. provided by Roche, Illumina or Applied Biosystems). In general, sequencing adaptors may be ligated to the (amplified) ligated DNA fragments. In case the linear or circularized fragment is amplified, by using for example PCR as described herein, the amplified product is linear, allowing the ligation of the adaptors. Suitable ends may be provided for ligating adaptor sequences (e.g. blunt, complementary staggered ends). Alternatively, primer(s) used for PCR or other amplification method, may include adaptor sequences, such that amplified products with adaptor sequences are formed in the amplification step g). In case the circularized fragment is not amplified, the circularized fragment may be fragmented, preferably by using for example a restriction enzyme in between primer binding sites for the inverse PCR reaction, such that DNA fragments ligated with the DNA fragment comprising the target nucleotide sequence remain intact. Sequencing adaptors may also be included in the steps c) and f) of the methods of the invention. These sequencing adaptors may be included as part of the adaptor sequences of the adaptors that may already optionally used in these steps and/or separate sequence adaptors may be provided in these steps in addition, Preferably long reads may be generated in the high throughput sequencing method used. Long reads may allow to read across multiple DNA fragments of ligated DNA fragments. This way, DNA fragments of step b) may be identified. DNA fragment sequences may be compared to a reference sequence and/or compared with each other. For example, as also explained hereafter, such DNA fragment sequences may be used for determining the the ratio of fragments of cells carrying a genetic mutation. By sequencing also DNA fragment sequences of DNA fragments adjacent to such sequences, unique ligated DNA fragments may be identified. This is in particular the case when DNA fragments were obtained in step b) by random fragmentation. The chance that two cells will provide for the exact same DNA fragment is very small, let alone that the DNA fragment ends to which such a fragment is ligated will be the same. Thus, by identifying DNA fragments this way, the ratio of cells and/or genomic regions of interest comprising a particular mutation may be determined.

Hence, it is not required to provide for a complete sequence of the ligated DNA fragments. It is preferred to at least sequence across (multiple) DNA fragments, such that DNA fragment sequences are determined.

It may also be contemplated to read even shorter sequences, for instance, short reads of 50-100 nucleotides. In such a scenario, it is preferred to fragment the (amplified) ligated DNA in smaller fragments, which may be subsequently ligated with an appropriate adaptor suitable for the high throughput sequencing method. In case a standard sequencing protocol would be used, this may mean that the information regarding the ligated DNA fragments may be lost. With short reads it may not be possible to identify a complete DNA fragment sequence. In case such short reads are contemplated, it may be envisioned to provide additional processing steps such that separate ligated DNA fragments when fragmented, are ligated or equipped with identifiers, such that from the short reads, contigs may be built for the ligated DNA fragments. Such high throughput sequencing technologies involving short sequence reads may involve paired end sequencing. By using paired end sequencing and short sequence reads, the short reads from both ends of a DNA molecule used for sequencing, which DNA molecule may comprise different DNA fragments, may allow coupling of DNA fragments that were ligated. This is because two sequence reads can be coupled spanning a relatively large DNA sequence relative to the sequence that was determined from both ends. This way, contigs may be built for the (amplified) ligated DNA fragments.

However, using short reads may be contemplated without identifying DNA fragments, because from the short sequence reads a genomic region of interest may be built, especially when the genomic region of interest has been amplified. Information regarding DNA fragments and/or separate genomic region of interests (for instance of a diploid cell) may be lost, but DNA mutations may still be identified.

Thus, the step of determining at least part of the sequence of the (amplified) ligated DNA sequence, may comprise short sequence reads, but preferably longer sequence reads are determined such that DNA fragment sequences may be identified. In addition, it may also be contemplated to use different high throughput sequencing strategies for the (amplified) (amplified) ligated DNA fragments, e.g. combining short sequence reads from paired end sequencing with the ends relatively far apart with longer sequence reads, this way, contigs may be build for the (amplified) ligated DNA fragments.

In one embodiment the invention may be used to provide for quality control of generated sequence information. In the analysis of the sequences as provided by a method of high throughput sequencing, sequencing errors may occur. A sequencing error may occur for example during the elongation of the DNA strand, wherein the wrong (i.e. non-complementary to the template) base is incorporated in the DNA strand. A sequencing error is different from a mutation, as the original DNA which is amplified and/or sequenced would not comprise that mutation. According to the invention, DNA fragment sequences may be determined, with (at least part of) sequences of DNA fragments ligated thereto, which sequences may be unique. The uniqueness of the ligated DNA fragments as they are formed in step c) may provide for quality control of the determined sequence in step h). When ligated DNA fragments are amplified, and sequenced at a sufficient depth, multiple copies of the same unique (ligated) DNA fragment (s) will be sequenced. Sequences of copies that originate from the same original ligated DNA fragment may be compared and amplification and/or sequencing errors may be identified.

Further Embodiments

Furthermore, according to the methods of the invention, from a sample of crosslinked DNA, the sequences of multiple genomic regions of interests are determined. For each genomic region of interest, a target nucleotide sequence is provided, for which corresponding primer(s) may be designed. The multiple genomic regions of interest may be genomic regions of interest that may also overlap, thereby increasing the size of which the sequence may be determined. For instance, in case a sequence of a genomic region of interest comprising a target nucleotide sequence typically would comprise 1 MB, combining partially overlapping genomic regions of interest, e.g. with an overlap of 0.1 MB, each with a corresponding target nucleotide sequence, combining 5 genomic regions of interest would result in a sequence of 4.6 MB (0.9+3*(0.1+0.8)+0.1+0.9=4.6 MB), thereby greatly extending the size of the genomic region of interest of which the sequence may be determined or otherwise analysed. Multiple target nucleotide sequences at defined distances within a genomic region of interest may also be used to increase the average coverage and/or the uniformity of coverage across the genomic region.

In addition, an identifier may be included in at least one of the oligonucleotide primers of step g). Identifiers may also be included in adaptor sequences, such as are used for ligation in between fragments during the ligation step c). By including an identifier in the oligonucleotide primer, when analysing a plurality of samples or a plurality of subsamples of crosslinked DNA simultaneously, the origin of each sample may easily be determined. (Sub)samples of crosslinked DNA may have been processed differently while the original sample of crosslinked DNA is the same, and/or samples of DNA may have been obtained for example from different organisms or patients. Identifiers allow to combine differently processed samples when the processing of samples may converge, e.g. identical procedural steps are performed. Such convergence of processing may in particular be advantageous when the sequencing step h) involves high throughput sequencing.

Prior to or after the amplification step g), according to the methods of the invention, a size selection step may be performed. Such a size selection step may be performed using gel extraction chromatography, gel electrophoresis or density gradient centrifugation, which are methods generally known in the art. Preferably DNA is selected of a size between 20-20,000 base pairs, preferable 50-10,000 base pairs, most preferably between 100-3,000 base pairs. A size separation stet allows to select for (amplified) ligated DNA fragments in a size range that may be optimal for PCR amplification and/or optimal for the sequence of long reads by next generation sequencing. Sequencing of reads of 500 nucleotides is currently commercially available, recent advance by companies such as the Single Molecule Real Time (SMRT™) DNA Sequencing technology developed by Pacific Biosciences (wide web at pacificbiosciences.com/) indicate the reads of 1,000 to 10,000 nucleotides are within reach.

In case the ploidy in a cell of a genomic region of interest is greater than 1, for each ploidy a contig is built in step h) of the methods according to the invention. Since the genomic environment of any given target site in the genome mostly consists of DNA genome sequences that are physically close to the target sequence on the linear chromosome template, it allows the reconstruction of each particular chromosome template. In case the ploidy of a genomic region of interest is greater than 1, multiple genomic regions of interest are present in a cell (or equivalent thereof). These multiple genomic regions of interest generally do not occupy the same space, i.e. they are separated in space. When a sample of crosslinked DNA of such a cell is fragmented, from each genomic region of interest in a cell a corresponding DNA fragment comprising the target nucleotide sequence will be formed. These DNA fragments will each ligate with DNA fragments in their proximity. Ligated DNA fragments will thus be representative of the different genomic regions of interest. For instance, in case the ploidy is two, when two fragments each having a unique mutation, and separated by 1 MB, would be found together in ligated DNA fragments, it may be concluded that these two fragments are from the same genomic region of interest. Thus, in this scenario, two fragments were identified, and are both assigned to the same genomic region. Thus, when building a contig from the sequences of identified fragments, these two fragments carrying a mutation would be used for building a contig for one particular genomic region, while the contig built for the other genomic region would not carry the mutations.

Thus, according to the methods of the invention, the step h) of building a contig comprises the steps of:
1) identifying the fragments of step b);
2) assigning the fragments to a genomic region;
3) building a contig for the genomic region from the sequences of the fragments.

Also, when three fragments comprising a unique mutation occur (A*, B* and C*) and the ploidy of the genomic interest is two. This time, ligation products comprising two of the mutated fragments are identified, one ligation product comprising A*B* and one with A*C*. Also ligation products comprising non-mutated, fragments are identified BC and AC. In this scenario, the ligated DNA fragments A*B and A*C* are coupled by fragment A*, and ligated DNA fragments BC and AC are coupled by fragment C. In this scenario DNA fragments A*, B* and C* are assigned to the same genomic region, while A, B and C are assigned to the other genomic region. Thus, accordingly, the step 2) of assigning the fragments to a genomic region comprises identifying the different ligation products and coupling of the different ligation products comprising the DNA fragments.

Likewise, the same would apply for heterogeneous cell populations. For instance, in case a sample of crosslinked DNA is provided which comprises a heterogeneous cell population (e.g. cells with different origin or cells from an organism which comprises normal cells and genetically mutated cells (e.g. cancer cells)), for each genomic region of interest corresponding to different genomic environment (which may e.g. be different genomic environments in a cell or different genomic environments from different cells) contigs may be built.

Identifying Mutations

In alternative embodiments, methods are provided for identifying the presence or absence of a genetic mutation.

In a first embodiment, a method is provided for identifying the presence or absence of a genetic mutation, comprising the steps a)-h) of any of methods of the invention as described above, wherein contigs are built for a plurality of samples, comprising the further steps of:
i) aligning the contigs of a plurality of samples;
j) identifying the presence or absence of a genetic mutation in the genomic regions of interest from the plurality of samples.

Alternatively, a method for identifying the presence or absence of a genetic mutation is provided, comprising the steps a)-g) of any of the methods of the invention as described above, comprising the further steps of:
i) aligning the contig to a reference sequence.
j) identifying the presence or absence of a genetic mutation in the genomic region of interest.

Genetic mutations can be identified for instance by comparing the contigs of multiple samples, in case one (or more) of the samples comprises a genetic mutation, this may be observed as the sequence of the contig is different when compared to the sequence of the other samples, i.e. the presence of a genetic mutation is identified. In case no sequence differences between contigs of the samples is observed, the absence of genetic mutation is identified. Alternatively, a reference sequence may also be used to which the sequence of a contig may be aligned. When the sequence of the contig of the sample is different from the sequence of the reference sequence, a genetic mutation is observed, i.e. the presence of a genetic mutation is identified. In case no sequence differences between the contig of the sample or samples and the reference sequence is observed, the absence of genetic mutation is identified.

It is not required to build a contig for identifying the presence or absence of a genetic mutation. As long as DNA fragments sequences may be aligned, with each other or with a reference sequence, the presence or absence of a genetic mutation may be identified. Thus, in alternative embodiments of the invention, a method is provided for identifying the presence or absence of a genetic mutation, according to any of the methods as described above, without the step h) of building a contig.

Such a method comprises the steps a)-g) of any of the methods as described above and the further steps of:
h) aligning the determined sequences of the (amplified) ligated DNA fragments to a reference sequence.
i) identifying the presence or absence of a genetic mutation in the determined sequences.

Alternatively, a method is provided for identifying the presence or absence of a genetic mutation, wherein of a plurality of samples sequences of (amplified) ligated DNA fragments are determined, comprising the steps a)-g) of any of the methods as described above, comprising the further steps of:
h) aligning the determined sequences of the (amplified) ligated DNA fragments of a plurality of samples.
i) identifying the presence or absence of a genetic mutation in the determined sequences.

Ratio of Alleles or Cells Carrying a Genetic Mutation

As already mentioned above, when from heterogeneous cell populations a sample of crosslinked DNA is provided (e.g. cells with different origin or cells from an organism which comprises normal cells and genetically mutated cells (e.g. cancer cells)), for each genomic region of interest corresponding to different genomic environment (which may e.g. be different genomic environments from different alleles in a cell or different genomic environments from different cells) contigs may be built. In addition, the ratio of fragments or ligated DNA fragments carrying a genetic mutation may be determined, which may correlate to the ratio of alleles or cells carrying the genetic mutation. The ligation of DNA fragments is a random process, the collection and order of DNA fragments that are part of the ligated DNA fragments may be unique and represent a single cell and/or a single genomic region of interest from a cell. Moreover, in case the fragmenting step b) comprises a random fragmentation process, such as e.g. sonication, the points at which the DNA has been broken may provide for an additional unique feature, especially within the context of the other DNA fragments to which it is ligated (which also may have unique fragment ends).

Thus identifying ligated DNA fragments comprising the fragment with the genetic mutation may also comprise identifying ligated DNA fragments with a unique order and collection of DNA fragments. The ratio of alleles or cells carrying a genetic mutation may be of importance in evaluation of therapies, e.g. in case patients are undergoing therapy for cancer. Cancer cells may carry a particular genetic mutation. The percentage of cells carrying such a mutation may be a measure for the success or failure of a therapy. In alternative embodiments, methods are provided for determining the ratio of fragments carrying a genetic mutation, and/or the ratio of ligated DNA fragments carrying a genetic mutation. In this embodiment, a genetic mutation is defined as a particular genetic mutation or a selection of particular genetic mutations.

In a first embodiment a method is provided for determining the ratio of fragments carrying a genetic mutation from a cell population suspected of being heterologous comprising the steps a)-h) of any of the methods as described above, comprising the further steps of:
i) identifying the fragments of step b);
j) identifying the presence or absence of a genetic mutation in the fragments;
k) determine the number of fragments carrying the genetic mutation;
l) determine the number of fragments not carrying the genetic mutation;
m) calculating the ratio of fragments carrying the genetic mutation.

In an alternative embodiment, a method is provided for determining the ratio of ligation products carrying a fragment with a genetic mutation from a cell population suspected of being heterologous comprising the steps a)-h) of any of the methods as described above, comprising the further steps of:
i) identifying the fragments of step b);
j) identifying the presence or absence of a genetic mutation in the fragments;
k) identifying the ligation products of step f) carrying the fragments with or without the genetic mutation;
l) determine the number of ligation products carrying the fragments with the genetic mutation;
m) determine the number of ligation products carrying the fragments without the genetic mutation;
n) calculating the ratio of ligation products carrying the genetic mutation.

In the methods of these embodiments, the presence or absence of a genetic mutation may be identified in step j) by aligning to a reference sequence and/or by comparing DNA fragment sequences of a plurality of samples.

In the methods according to the invention, an identified genetic mutation may be a SNP, single nucleotide polymorphism, an insertion, an inversion and/or a translocation. In case a deletion and/or insertion is observed, the number of fragments and/or ligation products from a sample carrying the deletion and/or insertion may be compared with a reference sample in order to identify the deletion and/or insertion. A deletion, insertion, inversion and/or translocation may also be identified based on the presence of chromosomal breakpoints in analyzed fragments.

In another embodiment, in the methods as described above, the presence or absence of methylated nucleotides is determined in DNA fragments, ligated DNA fragments, and/or genomic regions of interest. For example, the DNA of step a)-f) may be treated with bisulphite. Treatment of DNA with bisulphite converts cytosine residues to uracil, but leaves 5-methylcytosine residues unaffected. Thus, bisulphite treatment introduces specific changes in the DNA sequence that depend on the methylation status of individual cytosine residues, yielding single-nucleotide resolution information about the methylation status of a segment of DNA. By dividing samples into subsamples, wherein one of the samples is treated, and the other is not, methylated nucleotides may be identified. Alternatively, sequences from a plurality of samples treated with bisulphite may also be aligned, or a sequence from a sample treated with bisulphite may be aligned to a reference sequence.

When analyzing (short) sequence reads, it may be of interest to prevent sequencing the primers used. Thus, in an alternative method, the primer sequence may be removed prior to the high throughput sequencing step. Thus, in an alternative embodiment, the following method is provided for determining the sequence of a genomic region of interest comprising a target nucleotide sequence, comprising the steps of:
a) providing a sample of cross-linked DNA;
b) fragmenting the crosslinked DNA;
c) ligating the fragmented crosslinked DNA;
d) reversing the crosslinking;
e) optionally fragmenting the DNA of step d), preferably with a restriction enzyme;
f) optionally, ligating the fragmented DNA of step d) or e) to at least one Adaptor;
g) amplifying the ligated DNA fragments of step d) or e) comprising the target nucleotide sequence using at least one primer that preferably contains a 5' overhang carrying a type III restriction enzyme recognition site and (2) hybridises to the target nucleotide sequence, or amplifying the ligated DNA fragments of step f) using at least one primer that (1) preferably contains a 5' overhang carrying a type III restriction enzyme recognition site and (2) hybridises to the target nucleotide sequence and at least one primer which hybridises to the at least one adaptor;
h) digesting the amplified nucleotide sequences of interest with a type III restriction enzyme, followed by a size selection step to remove the released double-strand primer sequences;
i) fragmenting the DNA, preferably by sonication,
j) optionally, ligating double-stranded adaptor sequences needed for next generation sequencing
k) determining at least part of the sequence of the (amplified) ligated DNA fragments of step d), e), f) or g) comprising the target nucleotide sequence preferably using high throughput sequencing;
l) identifying genetic variation in, and building a contig of, the genomic region of interest from the determined sequences.

In an alternative embodiment, in any of the methods as described herein, in step g) primers are used carrying a moiety, e.g. biotin, for the optional purification of (amplified) ligated DNA fragments through binding to a solid support.

In one embodiment, the ligated DNA fragments comprising the target nucleotide sequence may be captured with a hybridisation probe (or capture probe) that hybridises to a target nucleotide sequence. The hybridisation probe may be attached directly to a solid support, or may comprise a moiety, e.g. biotin, to allow binding to a solid support suitable for capturing biotin moieties (e.g. beads coated with streptavidin). In any case, the ligated DNA fragments comprising a target nucleotide sequence are captured thus allowing to separate ligate DNA fragments comprising the target nucleotide sequence from ligated DNA fragments not comprising the target nucleotide sequence. Hence, such a capturing steps allows to enrich for ligated DNA fragments comprising the target nucleotide sequence. Hence, wherein throughout the invention, an amplification step is performed, which is also an enrichment step, alternatively a capture step with a probe directed to a target nucleotide sequence may be performed. For a genomic region of interest at least one capture probe for a target nucleotide sequence may be used for capturing. For a genomic region of interest more than one probe may be used for multiple target nucleotide sequences. For example, similar to as described for the BRCA1 gene, one primer of one of the 5 target nucleotide sequences may be used as a capture probe (A, B, C, D or E). Alternatively, the 5 primers may be used in a combined fashion (A, B, C, D and E) capturing the genomic region of interest.

In one embodiment an amplification step and capture step may be combined, e.g. first performing a capture step and than an amplification step or vice versa.

In one embodiment, a capture probe may be used that hybridises to an adaptor sequence comprised in (amplified) ligated DNA fragments.

Example

This is an example of a whole gene sequencing approach according to the invention that was used to determine the complete Brca1 gene sequence. The cells that were used were SUM149PT cells, a breast cancer adherent cell-line, with a deletion of a T at the 2288 position in Brca1 locus (Elstrodt et al. Cancer Res, 2006). FIG. 1 shows a schematic of the method.

Cell Culturing

SUM149PT cells are cultured in 150 cm2 dishes up to full plates with RPMI/10% FCS/penstrep. Prior splitting and counting of a dish showed that a full 150 cm2 dish contains ~20×106 SUM149PT cells.

Fixation and Cell Lysis

Cultured cells are washed with PBS and fixated with PBS/10% FCS/2% formaldehyde for 10 minutes at RT. The cells are subsequently washed and collected, and taken up in lysis buffer
(50 mM Tris-HCl pH7.5, 150 mM NaCl, 5 mM EDTA, 0.5% NP-40, 1% TX-100 and 1X Complete protease inhibitors (Roche #11245200) and incubate 10 minutes on ice. Cells are subsequently washed and taken up in MilliQ Fragmenting 1: Digestion The fixated lysed cells are digested with NIaIII (New England Biolabs # R0125).

Ligating 1

The NIaIII enzyme is heat-inactivated and subsequently a ligation step is performed using T4 DNA Ligase (Roche, #799009).

Reversing Cross-Linking

To the sample, Prot K (10 mg/ml) is added and incubated at 65° C. RNase A (10 mg/ml, Roche #10109169001) is subsequently added and the sample is incubated at 37° C. Next, phenol-chloroform extraction is performed, and the supernatant comprising the DNA is precipitated and pelleted. The pellet is dissolve in 10 mM Tris-HCl pH 7.5.

Fragmenting 2: Second Digestion

The digested and ligated sample is digested with Nspl (New England Biolabs # R0602S).

Ligating 2: Second Ligation and Purification

To the sample, Prot K (10 mg/ml) is added and incubated at 65° C. RNase A (10 mg/ml, Roche #10109169001) is subsequently added and the sample is incubated at 37° C. Next, phenol-chloroform extraction is performed, and the supernatant comprising the DNA is precipitated and pelleted. The pellet is dissolved in 10 mM Tris-HCl pH 7.5. The enrichment-template is now finished and can be stored or continued with directly.

Amplifying Ligated DNA Fragments: PCR

The primers used for the PCR-enrichment of the Brca1 locus are designed as inverted unique primers nearby (<50 bp) the restriction sites of an NIaIII restriction fragment with a spacing of the primersets, i.e. 'viewpoints', of approximately 20 kb (see FIG. 2 and table 1).

TABLE 1 overview of primer sequences used.
Primers are named (name) with reference to the BRCA1 gene, the position on the sequence map (e.g. 50.1 (kb)) and being a forward (fw) or reverse (rev) primer. vp indicates the viewpoints, ID indicates the SEQ ID No., i.e. SEQ ID Nos. 1-10. The sequence of the BRCA1 gene to which the primer corresponds is also indicated (start(5') and end(3')), please note that the primers are in outward orientation, i.e. inverse, they cannot form an amplicon using normal DNA as a template.

| name | vp | ID | sequence | start(5') | end(3') |
|---|---|---|---|---|---|
| BRCA1_9.9_fw | A | 1 | CTGGTGGGATCTGTCATTT | 6470734 | 6470752 |
| BRCA1_9.9_rev | A | 2 | TGGTAGCAAACACTTCCAC | 6470481 | 6470463 |
| BRCA1_28.9_fw | B | 3 | TATAAGTTTGCCTGCTGCAC | 6489743 | 6489762 |
| BRCA1_28.9_rev | B | 4 | TTTCCTTAACAATGCACAAA | 6489413 | 6489394 |
| BRCA_50.1_fw | C | 5 | CATTACTGTAGAAGTTCCCTAAA | 6511331 | 6511353 |
| BRCA_50.1_rev | C | 6 | ACCATTGCTGTTCCTTCTAA | 6510682 | 6510663 |
| BRCA_65.2_fw | D | 7 | TCCTCCTGAAGAGAAACTTG | 6526103 | 6526122 |
| BRCA_65.2_rev | D | 8 | AGTTCCCACCTTGAAGAATC | 6525783 | 6525764 |
| BRCA_91.5_fw | E | 9 | AGTGAGCGCCGAATTTGC | 6552296 | 6552313 |
| BRCA_91.5_rev | E | 10 | GCGAAGACCTTTCATTCC | 6552022 | 6552005 |

A typical enrichment-PCR reaction consist of 25 µl:
2.5 µl 10X PCR buffer 3 (supplied with the Expand Long Template Polymerase)
0.5 µl dNTP (10 mM)
0.5 µl forward primer (of a 1/7 dilution from a 1 µg/µl primer stock)
0.5 µl reverse primer (of a 1/7 dilution from a 1 µg/µl primer stock)
0.375 µl Expand Long Template Polymerase (Roche #11759060001)
100 ng of enrichment-template
X µl Milli-Q to a total volume of 25 µl Sequencing the Amplified Ligated DNA Fragments Proceed with library preparation for SOLiD sequencing, according to standard SOLiD protocols.

Results

The read distribution from the different viewpoints was highest around the site of the viewpoint. Further statistics are shown in table 2. Sequence reads from the viewpoint libraries C, D and E identified the 2288delT mutation. It was also determined which sequences of the BRCA1 gene were not covered, from viewpoint A, 15807 basepairs were not covered, from B, 50124 b. From C, D, and E all the BRCA1 sequences were covered.

TABLE 2

The sequence read statistics per viewpoint.

| vp | M | TR | % MtT | mean | median | % nt 20x |
|---|---|---|---|---|---|---|
| A | 898515 | 13715420 | 6.55 | 531 | 3 | 11.5 |
| B | 17578 | 7401964 | 0.24 | 10 | 0 | 4.90 |
| C | 2098974 | 11190246 | 18.76 | 1241 | 29 | 63 |
| D | 3113059 | 9851741 | 31.60 | 1840 | 45 | 74.70 |
| E | 134324 | 9108300 | 1.47 | 79 | 42 | 71.70 |

The sequence read statistics per viewpoint library (vp, A-E) are indicated.
M (reads matched to BRCA1),
TR (total number of reads),
% MtT (% of total reads matched to target),
mean (mean coverage),
median (median coverage),
% nt 20x (the % of nucleotides from the BRCA1 gene that has been more than 20 times coverage).

Thus, from the single viewpoints C, D and E, the complete BRCA1 of 100 kb was covered, from the A viewpoint 85 kb of the BRCA1 gene was covered, from the B viewpoint 50 kb of the BRCA1 gene was covered and from the C, D and E viewpoints the 2288delT mutation was confirmed.

The invention claimed is:

1. A method of generating one or more contigs of one or more genomic regions of interest, the method comprising:
   a) providing a DNA sample comprising protein and at least 1000 DNA molecules each comprising the one or more genomic regions of interest,
      wherein each genomic region of interest comprises one or more target polynucleotide sequences and DNA sequence in addition to the one or more target polynucleotide sequences, and
      wherein each of the one or more target polynucleotide sequences is of sufficient length to distinguish a nucleotide sequence comprising the target polynucleotide sequence from the other nucleotide sequences in the DNA molecules,
   b) treating the DNA sample with formaldehyde to crosslink the one or more genomic regions of interest,
   c) fragmenting the crosslinked genomic regions to generate crosslinked DNA fragments of the one or more genomic regions of interest having ligatable ends, wherein a set of the crosslinked DNA fragments comprises at least one target nucleotide sequence,
   d) ligating the crosslinked DNA fragments to produce ligated DNA products of at least 100 bp in length and comprising at least three overlapping and/or directly flanking DNA fragments from the one or more genomic regions of interest in addition to a DNA fragment comprising the one or more target polynucleotide sequences,
   e) reversing the crosslinking;
   f) optionally, specifically amplifying the ligated DNA products to produce amplification products,
   g) sequencing the ligated products, or amplification products thereof, so as to generate at least 17578 sequences of at least 20 base pairs in length, wherein the sequences comprise overlapping and/or directly flanking sequences of the at least three overlapping and/or directly flanking DNA fragments, wherein at least 4.9% of the nucleotides directly corresponding to the individual nucleotides of each of the one or more genomic regions of interest has been sequenced at least 20 times, and wherein the sequences are sufficient to build a contig of at least one of the one or more genomic regions of interest, and h) aligning, with a computer program, the at least 17578 sequences to one or more reference sequences comprising at least one of the one or more genomic regions of interest to generate one or more contigs of at least one of the one or more genomic regions of interest, wherein the one or more contigs are generated utilizing the overlapping and/or directly flanking sequences of the at least three overlapping and/or directly flanking DNA fragments.

2. The method according to claim 1, further comprising circularising the DNA after reversing the crosslinking.

3. The method according to claim 1, wherein more than one target polynucleotide sequence for at least one of the one or more genomic regions of interest is provided.

4. The method according to claim 1, wherein fragmenting comprises sonication, followed by enzymatic DNA end repair.

5. The method according to claim 4, wherein the ligation is performed in the presence of an adaptor, ligating adaptor sequences in between fragments.

6. The method according to claim 1, wherein fragmenting comprises fragmenting with a restriction enzyme.

7. The method according to claim 6, wherein, during fragmentation, a plurality of subsamples are fragmented, and for each subsample restriction enzymes with different recognition sites are used.

8. The method according to claim 6, wherein the ligation is performed in the presence of an adaptor, ligating adaptor sequences in between fragments.

9. The method according to claim 1, wherein prior to or after the amplification, a size selection step is performed.

10. The method according to claim 9, wherein the size selection step is performed utilizing gel extraction chromatography, gel electrophoresis or density gradient centrifugation.

11. The method according to claim 9, wherein DNA is selected of a size at least 100 base pairs.

12. The method according to claim 1 wherein the ploidy of at least one of the one or more genomic regions of interest is greater than 1, and wherein a contig is provided for each ploidy.

13. The method according to claim 1, wherein a comparison of the sequence of the contig to a reference sequence of the genomic region of interest demonstrates the presence or absence of a genetic mutation in the one or more genomic regions of interest.

14. The method according to claim 1, further comprising capturing the ligated DNA products or amplification products thereof with a capture probe that is specific to at least one of the one or more target polynucleotide sequences so as to separate the ligated DNA products from ligated DNA products or amplification products not comprising the one or more target polynucleotide sequences.

15. The method according to claim 1, further comprising, after reversing the crosslinking, ligating the ligated DNA products to at least one adaptor.

16. A method of generating one or more contigs of one or more genomic regions of interest, the method comprising:
a) providing a DNA sample comprising protein and at least 1000 DNA molecules each comprising the one or more genomic regions of interest,
wherein each genomic region of interest comprises one or more target polynucleotide sequences and DNA sequence in addition to the one or more target polynucleotide sequences, and
wherein each of the one or more target polynucleotide sequences is of sufficient length to distinguish a nucleotide sequence comprising the target polynucleotide sequence from the other nucleotide sequences in the DNA molecules,
b) treating the DNA sample with formaldehyde to crosslink the one or more genomic regions of interest,
c) fragmenting the crosslinked genomic regions to generate crosslinked DNA fragments of the one or more genomic regions of interest having ligatable ends, wherein a set of the crosslinked DNA fragments comprises at least one target nucleotide sequence,
d) ligating the crosslinked DNA fragments to produce ligated DNA products of at least 100 bp in length and comprising at least three overlapping and/or directly flanking DNA fragments from the one or more genomic regions of interest in addition to a DNA fragment comprising the one or more target polynucleotide sequences,
e) reversing the crosslinking;
f) optionally, specifically amplifying the ligated DNA products to produce amplification products,
g) sequencing the ligated products, or amplification products thereof, so as to generate at least 17578 sequences of at least 20 base pairs in length, wherein the sequences comprise overlapping and/or directly flanking sequences of the at least three overlapping and/or directly flanking DNA fragments, wherein at least 4.9% of the nucleotides directly corresponding to the individual nucleotides of each of the one or more genomic regions of interest has been sequenced at least 20 times, and wherein the sequences are sufficient to build a contig of at least one of the one or more genomic regions of interest, and
h) aligning, with a computer program, the at least 17578 sequences to generate one or more contigs of at least one of the one or more genomic regions of interest, wherein the one or more contigs are assembled utilizing the overlapping and/or directly flanking sequences of the at least three overlapping DNA fragments and wherein the overlaps of the at least three overlapping DNA fragments are sufficient to assemble the one or more contigs.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Homo sapiens

<400> SEQUENCE: 1
ctggtgggat ctgtcattt                                                  19

<210> SEQ ID NO 2
<211> LENGTH: 19
<212> TYPE: DNA
<213> ORGANISM: Homo sapiens

<400> SEQUENCE: 2
tggtagcaaa cacttccac                                                  19

<210> SEQ ID NO 3
<211> LENGTH: 20
<212> TYPE: DNA
<213> ORGANISM: Homo sapiens

<400> SEQUENCE: 3
tataagtttg cctgctgcac                                                 20

<210> SEQ ID NO 4
<211> LENGTH: 20
<212> TYPE: DNA
<213> ORGANISM: Homo sapiens

<400> SEQUENCE: 4
tttccttaac aatgcacaaa                                                 20

<210> SEQ ID NO 5
<211> LENGTH: 23
<212> TYPE: DNA
<213> ORGANISM: Homo sapiens
```

```
<400> SEQUENCE: 5
cattactgta gaagttccct aaa                                              23

<210> SEQ ID NO 6
<211> LENGTH: 20
<212> TYPE: DNA
<213> ORGANISM: Homo sapiens

<400> SEQUENCE: 6
accattgctg ttccttctaa                                                  20

<210> SEQ ID NO 7
<211> LENGTH: 20
<212> TYPE: DNA
<213> ORGANISM: Homo sapiens

<400> SEQUENCE: 7
tcctcctgaa gagaaacttg                                                  20

<210> SEQ ID NO 8
<211> LENGTH: 20
<212> TYPE: DNA
<213> ORGANISM: Homo sapiens

<400> SEQUENCE: 8
agttcccacc ttgaagaatc                                                  20

<210> SEQ ID NO 9
<211> LENGTH: 18
<212> TYPE: DNA
<213> ORGANISM: Homo sapiens

<400> SEQUENCE: 9
agtgagcgcc gaatttgc                                                    18

<210> SEQ ID NO 10
<211> LENGTH: 18
<212> TYPE: DNA
<213> ORGANISM: Homo sapiens

<400> SEQUENCE: 10
gcgaagacct ttcattcc                                                    18
```